United States Patent
Gaddy et al.

(10) Patent No.: US 8,592,190 B2
(45) Date of Patent: Nov. 26, 2013

(54) METHODS FOR SEQUESTERING CARBON DIOXIDE INTO ALCOHOLS VIA GASIFICATION FERMENTATION

(75) Inventors: James L. Gaddy, Fayeteville, AR (US); Ching-Whan Ko, Fayetteville, AR (US); J. Randy Phillips, Springdale, AR (US); M. Sean Slape, Fayetteville, AR (US)

(73) Assignee: Ineos Bio Limited, Lisle, IL (US)

( * ) Notice: Subject to any disclaimer, the term of this patent is extended or adjusted under 35 U.S.C. 154(b) by 647 days.

(21) Appl. No.: 12/456,049

(22) Filed: Jun. 11, 2009

(65) Prior Publication Data

US 2010/0317077 A1  Dec. 16, 2010

(51) Int. Cl.
| | |
|---|---|
| C12P 7/04 | (2006.01) |
| C12P 7/06 | (2006.01) |
| C12P 7/08 | (2006.01) |
| C12P 7/10 | (2006.01) |
| C12P 7/16 | (2006.01) |

(52) U.S. Cl.
USPC ........... 435/157; 252/373; 435/160; 435/161; 435/163; 435/165

(58) Field of Classification Search
USPC .......... 252/373; 435/157, 162, 165, 161, 163, 435/160
See application file for complete search history.

(56) References Cited

U.S. PATENT DOCUMENTS

| | | | |
|---|---|---|---|
| 3,976,442 A | 8/1976 | Paull et al. | |
| 4,017,271 A | 4/1977 | Barclay et al. | |
| 4,334,026 A * | 6/1982 | Chynoweth et al. | 435/163 |
| 4,351,905 A | 9/1982 | Clyde | |
| 4,353,713 A * | 10/1982 | Cheng | 48/202 |
| 4,393,136 A | 7/1983 | Cheetham | |
| 4,400,470 A | 8/1983 | Zeikus et al. | |
| 4,654,123 A | 3/1987 | Berg et al. | |
| 4,720,289 A * | 1/1988 | Vaugh et al. | 48/197 R |
| 4,737,459 A | 4/1988 | Zeikus et al. | |
| 4,886,751 A | 12/1989 | Thorsson | |
| 4,933,283 A * | 6/1990 | Chen et al. | 435/166 |
| 5,173,429 A | 12/1992 | Gaddy et al. | |
| 5,182,199 A | 1/1993 | Hartley | |
| 5,593,886 A | 1/1997 | Gaddy | |
| 5,807,722 A | 9/1998 | Gaddy | |
| 5,821,111 A | 10/1998 | Grady | |

(Continued)

FOREIGN PATENT DOCUMENTS

| | | |
|---|---|---|
| EP | 0 253 540 A1 | 1/1988 |
| EP | 0 444 684 A2 | 9/1991 |

(Continued)

OTHER PUBLICATIONS

Thorsson, "Process for Producing Ethanol by Fermenting Molasses," English abstract of Hungarian Patent No. HU 201971-B.

(Continued)

Primary Examiner — Wayne Langel
(74) Attorney, Agent, or Firm — Vikrant B. Pancha; Ineos Bio SA

(57) ABSTRACT

The present invention is directed to improvements in gasification for use with synthesis gas fermentation. Further, the present invention is directed to improvements in gasification for the production of alcohols from a gaseous substrate containing at least one reducing gas containing at least one microorganism.

8 Claims, 8 Drawing Sheets comprises embodiments of the present invention providing a graphic illustration of total ethanol produced versus CO2 added comparing multiple stage gasifier data and single stage gasifier data

(56) References Cited

U.S. PATENT DOCUMENTS

| | | | |
|---|---|---|---|
| 6,136,577 A | 10/2000 | Gaddy | |
| 6,340,581 B1 | 1/2002 | Gaddy | |
| 6,919,488 B2 | 7/2005 | Melnichuk et al. | |
| 7,285,402 B2* | 10/2007 | Gaddy et al. | 435/161 |
| 7,919,290 B2* | 4/2011 | Offerman et al. | 435/161 |
| 8,354,564 B2* | 1/2013 | Brown et al. | 568/913 |
| 8,383,376 B2* | 2/2013 | Simpson et al. | 435/157 |
| 8,507,228 B2* | 8/2013 | Simpson et al. | 435/132 |
| 2003/0211585 A1* | 11/2003 | Gaddy et al. | 435/161 |
| 2008/0213848 A1* | 9/2008 | Gaddy et al. | 435/161 |
| 2009/0215139 A1* | 8/2009 | Datta et al. | 435/162 |
| 2010/0065781 A1* | 3/2010 | Brothier | 252/373 |
| 2010/0090167 A1* | 4/2010 | Fournier et al. | 252/373 |
| 2010/0125107 A1* | 5/2010 | Lee et al. | 518/702 |
| 2010/0129691 A1* | 5/2010 | Dooher et al. | 429/17 |
| 2010/0224835 A1* | 9/2010 | Chornet et al. | 252/373 |
| 2010/0270505 A1* | 10/2010 | Gallaspy et al. | 252/373 |
| 2010/0270506 A1* | 10/2010 | Goetsch et al. | 252/373 |
| 2010/0273899 A1* | 10/2010 | Winter | 518/703 |
| 2010/0283009 A1* | 11/2010 | Nickels et al. | 252/373 |
| 2011/0012064 A1* | 1/2011 | Al Chalabi et al. | 252/373 |
| 2011/0240923 A1* | 10/2011 | Sarkar et al. | 252/373 |
| 2012/0052541 A1* | 3/2012 | Oakley | 435/140 |
| 2012/0309066 A1* | 12/2012 | Simpson et al. | 435/140 |

FOREIGN PATENT DOCUMENTS

| | | |
|---|---|---|
| EP | 1 923 381 A1 | 5/2008 |
| GB | 711912 A | 7/1954 |
| WO | WO 98/00558 | 1/1998 |
| WO | WO 00/68407 | 11/2000 |
| WO | WO 02/08438 | 1/2002 |
| WO | WO 2007/042562 | 4/2007 |
| WO | WO 2007/123510 | 11/2007 |
| WO | WO 2008/028055 | 3/2008 |
| WO | WO 2008/033812 | 3/2008 |

OTHER PUBLICATIONS

Liou et al., "Clostridium carboxidivorans sp. nov., a Solvent-Producing Clostridium Isolated from an Agricultural Settling Lagoon, and Reclassification of the Acetogen Clostridium scatologenes strain SL1 as Clostridium drakei sp. nov.," Int. J. Sys. Evol. Microbiol., 55:2085-2091 (Sep. 2005).
Klasson et al., "Biological Production of Liquid and Gaseous Fuels from Synthesis Gas" Appl. Biochem. Biotechnol., Proceedings of the 11th Symposium on Biotechnology for Fuels and Chemicals, 24/25:857 (1990).
Phillips et al., "Biological Production of Ethanol from Coal Synthesis Gas-Medium Development Studies" Appl. Biochem. Biotechnol., Proceedings from the 14th Symposium on Biotechnology for Fuels and Chemicals, 39/40:559 (1993).
Rothstein et al., "Clostridium thermosaccharolyticum Strain Deficient in Acetate Production," J. Bacteriol, 165(1):319-320 (Jan. 1986).
Lovitt et al., "Ethanol Production by Thermophilic Bacteria: Biochemical Basis for Ethanol and Hydrogen Tolerance in Clostridium thermohydrosulfuricum," J. Bacteriol., 170(6):2809 (Jun. 1988).
Taherzadeh et al., "The Effects of Pantothenate Deficiency and Acetate Addition on Anaerobic Batch Fermentation of Glucose by Saccharomyces cerevisiae," Appl. Microbiol. Biotechnol., 46:176-182 (Sep. 1996).
Bahl et al., "Continuous Production of Acetone and Butanol by Clostridium acetobutylicum in a Two-Stage Phosphate Limited Chemostat," Eur. J. Appln. Microbiol. Biotechnol 15(4):201-205 (Oct. 1982).
Bahl et al., "Nutritional Factors Affecting the Ratio of Solvents Produced by Clostridium acetobutylicum," Appl. Environ. Microbiol., 52(1):169-172 (Jul. 1986).
Reardon et al., "Metabolic Pathway Rates and Culture Fluorescence in Batch Fermentations of Clostridium acetobutylicum," Biotechnol. Prog., 3(3):153-168 (Sep. 1987).

Terracciano et al., "Intracellular Conditions Required for Initiation of Solvent Production by Clostridium acetobutylicum," Appl. and Environ. Microbiol., 52(1):86-91 (Jul. 1986).
Long et al., "Sporulation of Clostridium acetobutylicum P262 in a Defined Medium," Appl. Environ. Microbiol., 45(4):1389-1393 (Apr. 1983).
Ferras et al., "Acetonobutylic Fermentation: Improvement of Performances by Coupling Continuous Fermentation and Ultrafiltration," Biotechnol. Bioengin.,28:523 (Apr. 1986).
Clarke et al., "Nature and Significance of Oscillatory Behaviour during Solvent Production by Clostridium acetobutylicum in Continuous Culture," Biotechnol. Bioengin., 32:538-544 (Aug. 1988).
Martin et al., "Effects of Acetic and Butyric Acids on Solvent Production by Clostridium acetobutylicum," Biotechnol. Lett., 5(20):89-94 (Feb. 1983).
Bryant et al., "Buffering as a Means for Increasing Growth and Butanol Production by Clostridium acetobutylicum," J. Indust. Microbiol., 3:49:55 (Feb. 1988).
Husemann et al., "Solventogenesis in Clostridium acetobutylicum Fermentations related to Carboxylic Acid and Proton Concentrations," Biotechnol. Bioengin., 32:843-852 (Sep. 1988).
Barik et al., "Biological Production of Alcohols from Coal through Indirect Liquefaction," Appl. Biochem. Biotechnol., Proceedings of the 9th Symposium on Biotechnol. for Fuels and Chemicals, 18:363 (1988).
Vega et al., "The Biological Production of Ethanol from Synthesis Gas," Appl. Biochem. Biotechnol., Proceedings of the 10th Symposium on Biotechnol. for Fuels and Chemicals, 20/21:781 (1989).
Landuyt et al., Transition from Acid Fermentation to Solvent Fermentatiaon in a Continuous Dilution Culture of Clostridium thermosaccharolyticum, Annals of New York Academy of Sciences, pp. 473-478 (Dec. 1987).
Lynd et al., "Thermophilic Ethanol Production," Appl. Biochem. Biotechnol., 28/29: 549 (1991).
Degraef et al., "The Steady-State Internal Redox State (NADH/NAD) Reflects the External Redox State and is Correlated with Catabolic Adaptation in Escherichia coli," J. Bacteriol., 181(8): 2351-2357 (Apr. 1999).
Hols et al., "Acetate Utilization in Lactococcus lactis Deficient in Dehydrogenase: A Rescue Pathway for Maintaining Redox Balance," J. Bacteriol., 181(17):5521 (Sep. 1999).
Rao et al., "Altered Electron Flow in a Reducing Environment in Clostridium acetobutylicum," Biotechnol. Lett., 10(2):129-132 (Feb. 1988).
Kim et al., "Redox Potential in Acetone-Butanol Fermentations," 9th Symposium on Biotechnology for Fuels and Chemicals, Boulder, CO (May 5-8, 1987).
Kim et al., "Electron Flow Shift in Clostridium acetobutylicum Fermentation by Electrochemically Introduced Reducing Equivalent," Biotechnol. Lett., 10(2):123-128 (Feb. 1988).
Phillips et al., "Synthesis Gas as Substrate for the Biological Production of Fuels and Chemicals," Appl. Biochem. and Biotechnol., Proceedings of the 15th Symposium on Biotechnology for Fuels and Chemicals, 45/46:145 (1994).
Rao et al., "Directed Metabolic Flow with High Butanol Yield and Selectivity in Continuous Culture of Clostridium acetobutylicum," Biotechnol. Lett., 10(5):313-318 (May 1988).
Rao et al., "Manipulation of End-Product Distribution in Strict Anaerobes," Annals of New York Academy of Science, pp. 76-83 (Nov. 1987).
Murray et al., "Ethanol Production by a Newly Isolated Anaerobe, Clostridium saccharolyticum: Effects of Culture Medium and Growth Conditions," Canad. J. Microbiol., 29:342 (Mar. 1983).
Ram et al., "Ethanol Production by Clostridium thermocellum SS8, A Newly Isolated Thermophilic Bacterium," Biotechnol. Lett., 11(8):589-592 (Aug. 1989).
Ingram et al., "Expression of Different Levels of Ethanologenic Enzymes from Zymomonas mobilis in Recombinant Strains of Escherichia coli," Appl. Environ. Microbiol., 54(2):397-404 (Feb. 1988).

(56) References Cited

OTHER PUBLICATIONS

Guedon et al., Carbon and Electron Flow in *Clostridium cellulolyticum* Grown in Chemostat on Synthetic Medium, J. Bacteriol., 181(10):3262-3269 (May 1999).

Grahame et al., "Substrate and Cofactor Reactivity of a Carbon Monoxide Dehyrogenase-Corrinoid Enzyme Complex: Stepwise Reduction of Iron-Sulfur and Corrinoid Centers, the Corrindoid Co2+/1+ Redox Midpoint Potential, and Overall Synthesis of Acetyl-CoA," Biochem., 32:10786-10793 (Oct. 12, 1993).

Gottwald et al., "The Internal pH of *Clostridium acetobutylicum* and its Effect on the Shift from Acid to Solvent Formation," Arch. Microbiol., 143:42-46 (Oct. 1985).

Examination Report dated Dec. 8, 2003, issued in counterpart European Patent Application No. 01954884.1

Examiner's Report dated Jul. 29, 2005, issued in counterpart Malaysian Patent Application No. PI20013724.

Younesi, Habibollah, "Ethanol and acetate production from synthesis gas via fermentation processes using anaerobic bacterium, *Clostridium ljungdahlii*", School of Chemical Engineering, Mar. 10, 2005; pp. 110 to 119.

Younesi, Habibollah, Liquid fuel production from synthesis gas via fermentation process in a continuous tank bioreactor (CSTBR) using *Clostridium ljungdahlii*, Iranian Journal of Biotechnology, vol. 4, No. 1, Jan. 2006, pp. 45-53.

\* cited by examiner

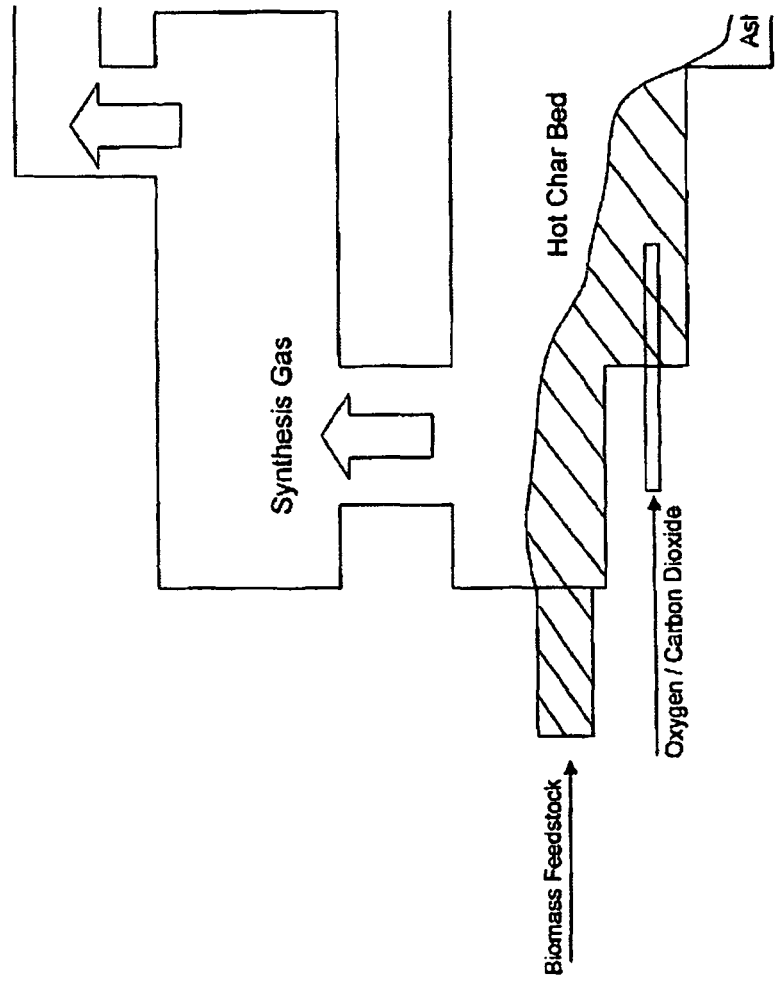
FIG. 1 Carbon Dioxide in Biomass Gasification Overall Process Flow (lower)

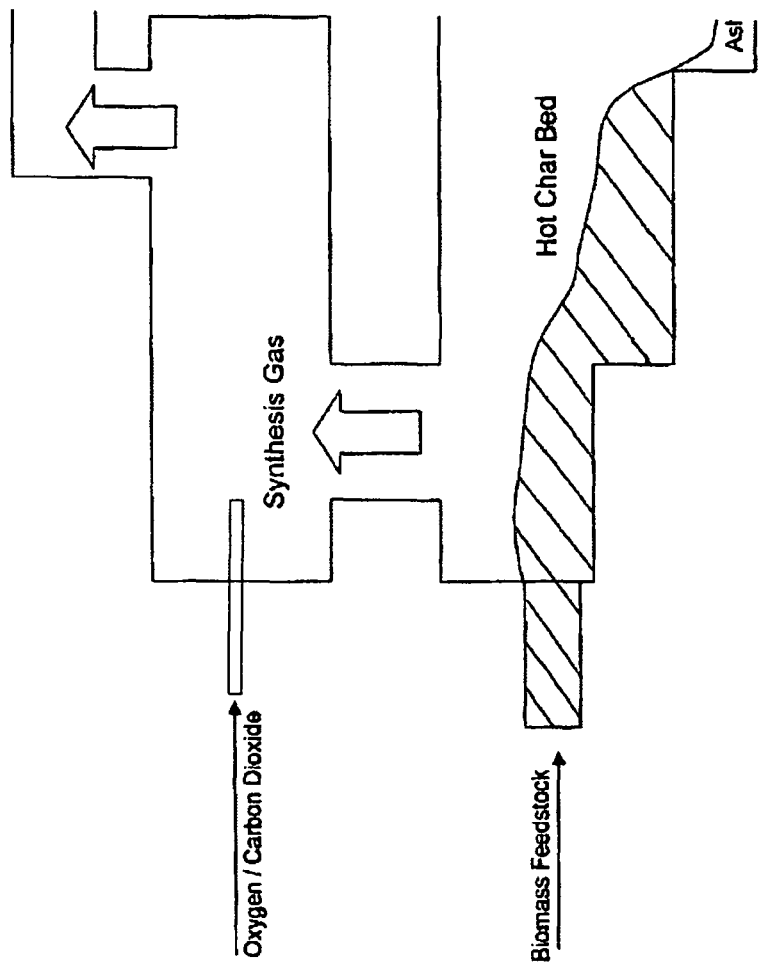
FIG. 2 Carbon Dioxide in Biomass Gasification Overall Process Flow (upper)

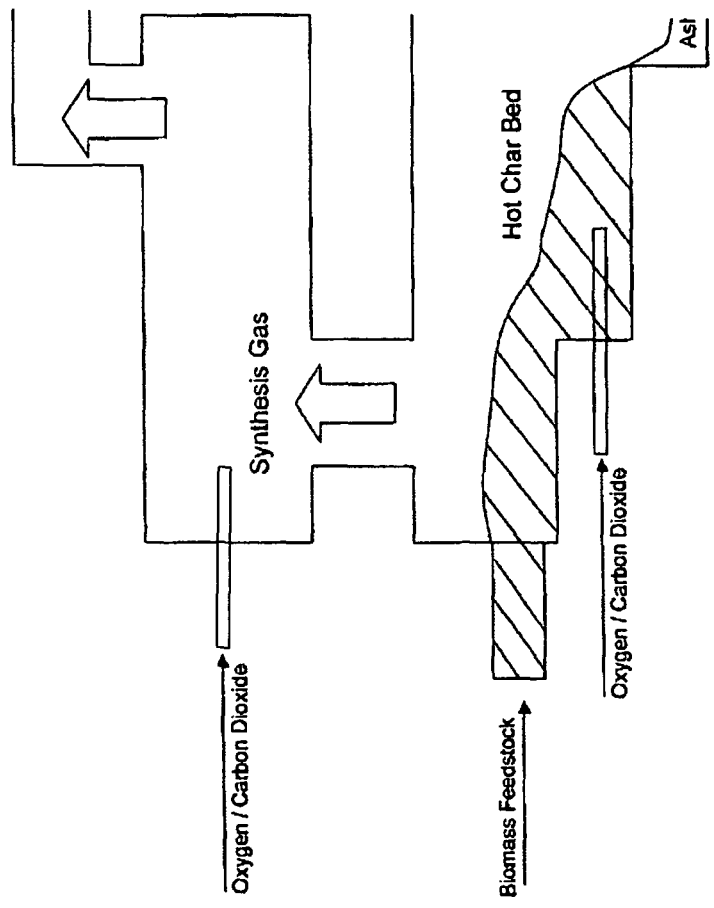
FIG. 3 Carbon Dioxide in Biomass Gasification Overall Process Flow (multiple)

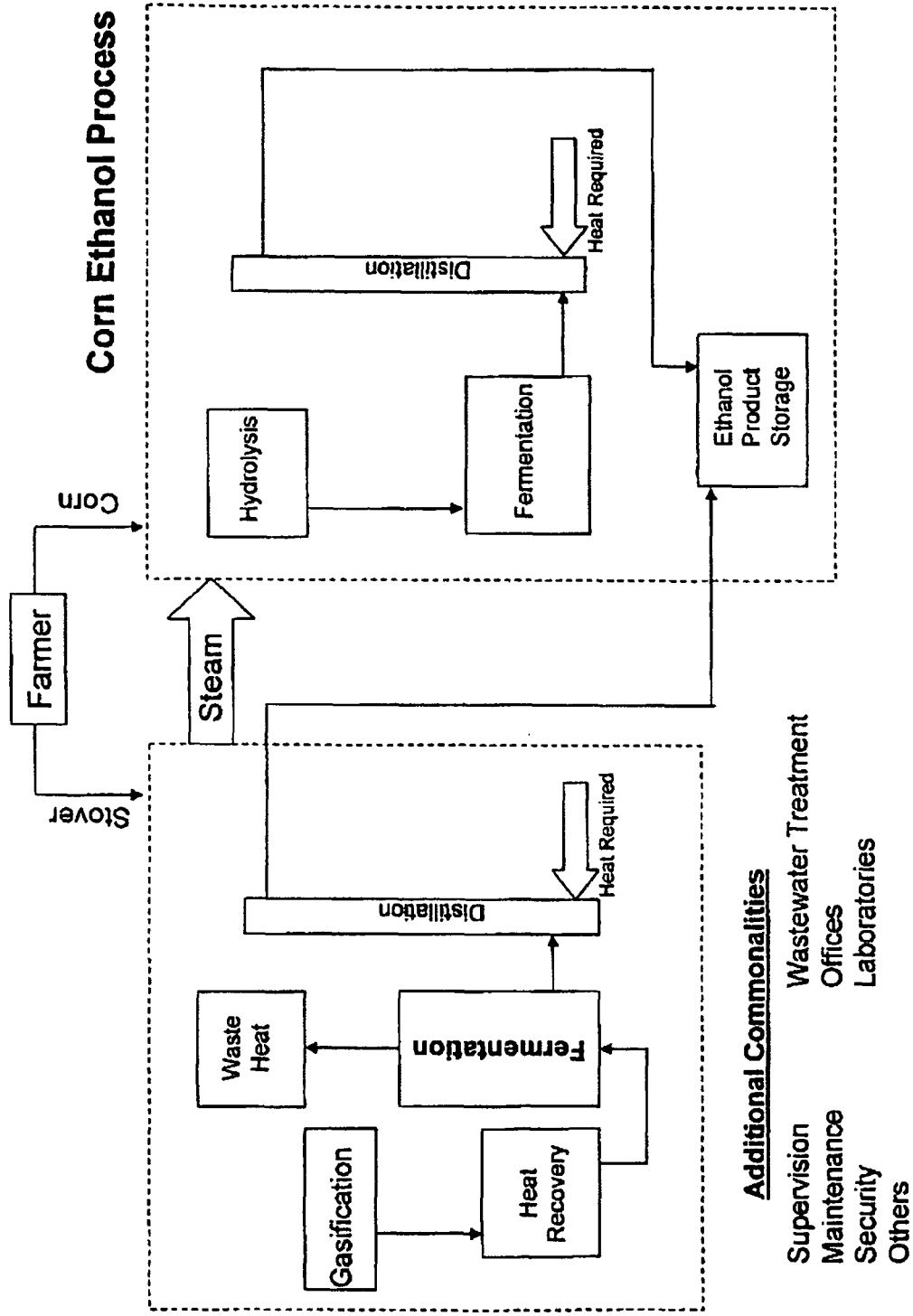
FIG. 4 comprises process synergies between the present invention and corn ethanol process.

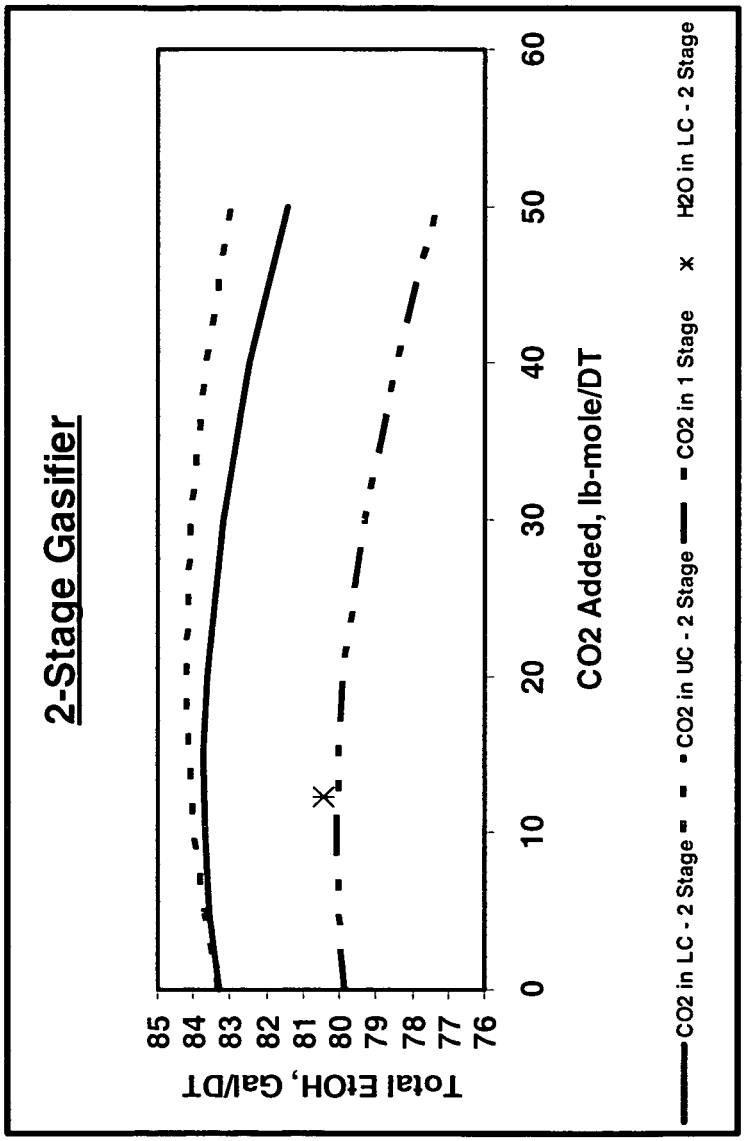
FIG. 5 comprises embodiments of the present invention providing a graphic illustration of total ethanol produced versus $CO_2$ added comparing multiple stage gasifier data and single stage gasifier data

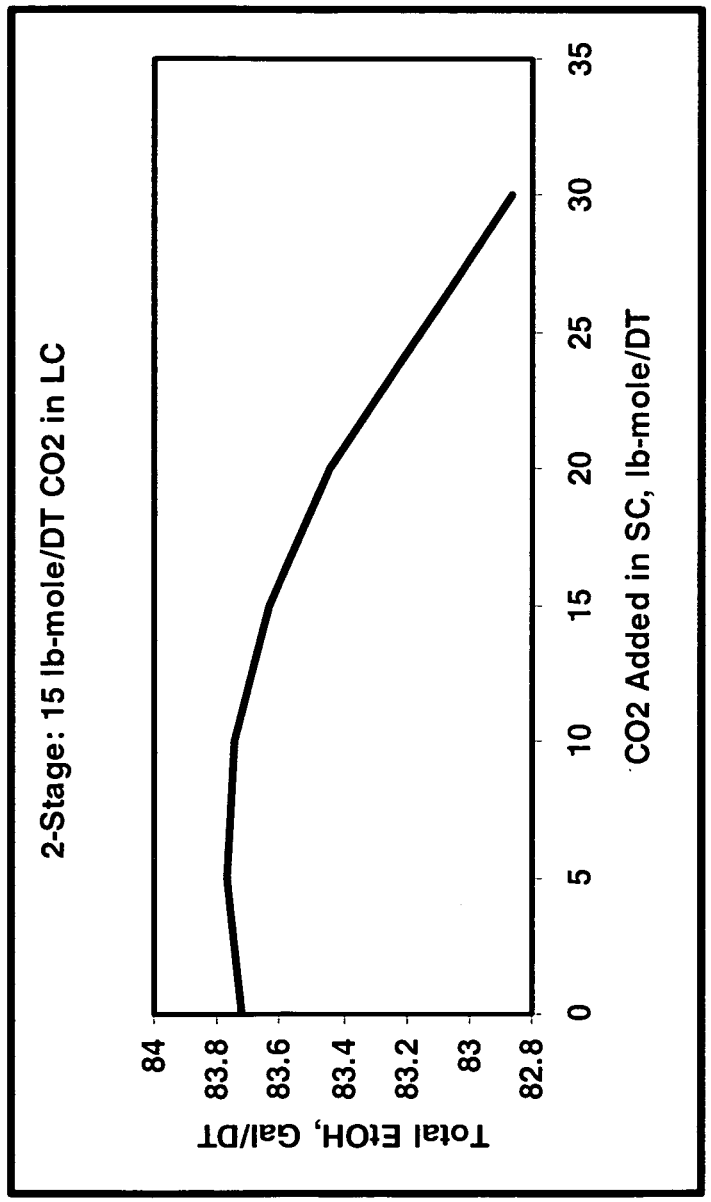
FIG. 6 comprises embodiments of the present invention providing a graphic illustration of total ethanol versus CO2 added

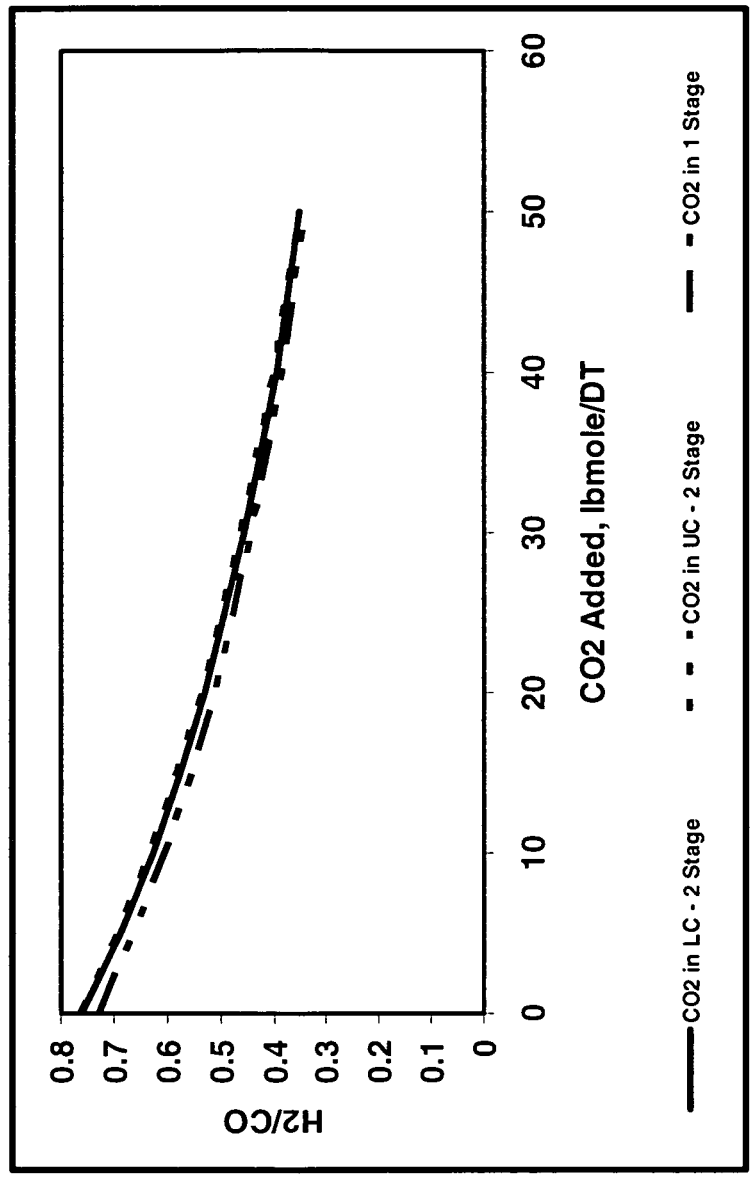

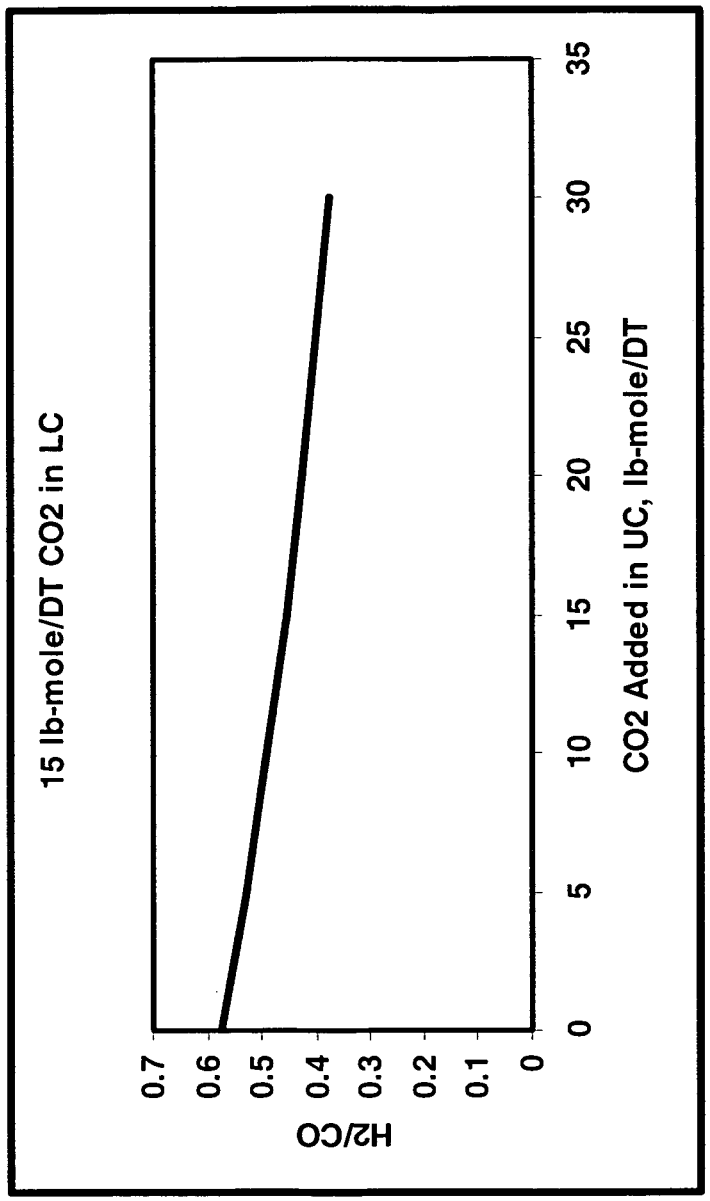
FIG. 8 comprises embodiments of the present invention providing a graphic illustration of H2/CO ratio versus CO2 added

METHODS FOR SEQUESTERING CARBON DIOXIDE INTO ALCOHOLS VIA GASIFICATION FERMENTATION

STATEMENT OF GOVERNMENT INTEREST

The present invention was developed in conjunction with U.S. Department of Energy Grant No. DE-FG36-04GO14315.

FIELD OF INVENTION

The present invention is directed to improvements in gasification for the production of alcohol from a gaseous substrate containing at least one reducing gas containing at least one microorganism.

BACKGROUND OF THE INVENTION

The present invention contemplates synthesis gas creation via gasification of carbonaceous materials producing a synthesis gas containing CO, $CO_2$, and $H_2$ that can be further acted upon by fermentation or digestion by certain microorganisms to produce alcohols (methanol, ethanol, propanol, butanol, etc.), acetic acid, acetates, hydrogen, etc. The following reactions and discussion are illustrative of an embodiment of the present invention involving alcohol production; which is used as the example product in the following description of the concept:

$$6CO + 3H_2O \rightarrow CH_3CH_2OH + 4CO_2 \quad (1)$$

$$6H_2 + 2CO_2 \rightarrow CH_3CH_2OH + 3H_2O \quad (2)$$

$$CO_2 + C \leftrightarrow 2CO \quad (3)$$

$$CO_2 + H_2 \leftrightarrow CO + H_2O \quad (4)$$

$$CH_4 + CO_2 \leftrightarrow 2CO + 2H_2 \quad (5)$$

The quantity of alcohols produced depends upon the efficiency of the gasification and fermentation processes. There exist many inefficiencies in gasification including various energy requirements involved in preparing carbonaceous feedstock, feeding carbonaceous feedstock, raising carbonaceous feedstock temperature, maintaining carbonaceous feedstock temperature, utilizing various oxygenates in each of the previous aspects of the present invention, inadequate oxygenate contact with carbonaceous feedstock, energy losses to the environment, endothermic reactions, air leakage in pressure units, and incomplete conversion of carbonaceous feedstock to CO and $H_2$. Use of low bulk density carbonaceous feedstock provide inefficiencies including: hot spots, over exposure to oxygenates, decreased CO concentrations, slagging of ash, etc. The type and quantity of oxygenate added can enable temperature control and increase alcohol production. These and other inefficiencies decrease the CO and $H_2$ available in the resultant synthesis gas which can negatively impact alcohol production.

The fermentation step can also negatively impact alcohol production via: incomplete conversion of CO or H2, incomplete utilization of CO or H2, undesirable byproduct production, undesirable byproduct induced inhibition, undesirable product induced inhibition, loss of cell mass, etc. Microorganisms, in some cases, participate in greater CO conversion than H2 conversion. Hence, higher CO concentrations can provide for greater alcohol production. For ethanol production from biomass using acetogenic bacteria, the ethanol production can be about 80 gallons per dry ton (gal/DT) of carbonaceous feedstock. Not utilized or unconverted carbon can remain as carbon dioxide.

It is believed that carbonaceous feedstock conversion to alcohols can assist in decreasing the carbon footprint on the environment. Alcohol production via the present invention can increase carbon utilization for fuel production; thus having a tremendous potential to positively impact climate change by improving the carbon efficiency. Further, the present invention provides a means to decrease dependence on foreign oil and increase global energy stability.

Carbon dioxide reforming is known in the art, however, converting carbonaceous material into fuel is still of technological significance and interest. The present invention applies to the gasification and/or fermentation process with the purpose of increasing the yield of alcohol (fermentation products) by Equations (1) to (5), as well as improving the efficiency of gasification of certain carbonaceous feedstock. The present invention also provides a means of reducing greenhouse gas emissions by sequestering the carbon into liquid transportation fuel alcohols; thus decreasing dependence on petrochemical fuel sources.

Gasification of corn stover and other biomass materials often result in excessive temperatures and melting of the ash (slagging), with no ready method for removal of this slag. This problem is particularly prevalent when using pure or enriched oxygen as the oxidant. In addition, when using biomass raw materials, the carbon monoxide composition of the synthesis gas is often quite dilute (especially with air as the oxidant), resulting in a low heating value and a less desirable gas for subsequent conversion to electricity, chemicals or fuels. Carbon dioxide is a global warming gas and is readily available from combustion processes or from certain chemical or biological reactions, such as production of ethanol via sugar fermentation from grain or cane. Carbon dioxide concentrations are increasing in the Earth's atmosphere as a result of fossil fuel consumption. A means of converting CO2 into liquid fuel could significantly assist reducing CO2 concentrations in the Earth's atmosphere and could aid in reducing CO2 emissions.

Grain and sugar cane ethanol processes require significant amounts of steam and electricity for feedstock preparation, ethanol purification, etc. As energy costs have increased, these items represent a major cost component in production of ethanol. Furthermore, during the harvesting of the grain or sugar cane, half or more of the crop is in the form of biomass, such as corn stover or sugar cane leaves and bagasse, which is largely unused. This biomass could be used to produce energy and or additional ethanol with the appropriate conversion process.

Various strains of acetogens (Drake, 1994) have been described for use in the production of liquid fuels from syngas: *Butyribacterium methylotrophicum* (Grethlein et al., 1990; Jain et al., 1994b); *Clostridium autoethanogenum* (Abrini et al., 1994); *Clostridium ljungdahlii* (Arora et al, 1995; Bank et al., 1988; Barik et al. 1990; and Tanner et al., 1993). Of these, *Clostridium ljungdahlii* and *Clostridium autoethanogenum* are known to convert CO to ethanol.

U.S. Pat. No. 5,173,429 to Gaddy et al. discloses *Clostridium ljungdahlii* ATCC No. 49587, an anaerobic microorganism that produces ethanol and acetate from CO and H.sub.2O and/or CO.sub.2 and H.sub.2 in synthesis gas.

U.S. Pat. No. 5,192,673 to Jain et al. discloses a mutant strain of *Clostridium* acetobytylicum and a process for making butanol with the strain.

U.S. Pat. No. 5,593,886 to Gaddy et al. discloses *Clostridium ljungdahlii* ATCC No. 55380. This microorganism can anaerobically produce acetate and ethanol using waste gas (e.g. carbon black waste gas) as a substrate.

U.S. Pat. No. 5,807,722 to Gaddy et al. discloses a method and apparatus for converting waste gases into useful products such as organic acids and alcohols using anaerobic bacteria, such as *Clostridium ljungdahlii* ATCC No. 55380.

U.S. Pat. No. 6,136,577 to Gaddy et al. discloses a method and apparatus for converting waste gases into useful products such as organic acids and alcohols (particularly ethanol) using anaerobic bacteria, such as *Clostridium ljungdahlii* ATCC Nos. 55988 and 55989.

U.S. Pat. No. 6,136,577 to Gaddy et al. discloses a method and apparatus for converting waste gases into useful products such as organic acids and alcohols (particularly acetic acid) using anaerobic strains of *Clostridium ljungdahlii*.

U.S. Pat. No. 6,753,170 to Gaddy et al. discloses an anaerobic microbial fermentation process for the production of acetic acid.

U.S. Pat. No. 7,285,402 to Gaddy et al. discloses an anaerobic microbial fermentation process for the production of alcohol.

Other strains of microorganisms have also been described for use in the production of liquid fuels from synthesis gas, e.g.: *Butyribacterium methylotrophicum* (Grethlein et al., 1990, Appl. Biochem. Biotech. 24/24:875-884); and *Clostridium autoethanogenum* (Abrini et al., 1994, Arch. Microbiol. 161:345-351).

Numerous conventional methods exist for gasification, synthesis gas creation, and synthesis gas fermentation. However, these methods suffer from numerous inefficiencies. There remains a need for additional more effective methods for gasification, additional more effective methods for gasification for use with synthesis gas, additional more effective methods for gasification for use with synthesis gas fermentation process, additional methods to effectively reduce $CO_2$ concentrations in the atmosphere, additional methods to effectively decrease $CO_2$ emissions, and additional methods to effectively sequester $CO_2$.

SUMMARY OF THE INVENTION

The present invention provides a method of optimizing synthesis gas production via gasification of carbonaceous material in a gasifier comprising: injecting carbon dioxide gas, oxygen gas, and carbonaceous material into a gasifier; creating syngas comprising carbon monoxide and hydrogen. The present invention provides for a method of producing alcohol comprising: injecting carbon dioxide gas, oxygen gas, and carbonaceous material into a gasifier; creating syngas comprising carbon monoxide and hydrogen; contacting syngas with biocatalyst in a fermentation container to produce an alcohol product mixture; selectively recovering alcohol from the product mixture. As an embodiment the present invention provides a method wherein said carbonaceous material comprises selection from: carbonaceous material, carbonaceous municipal solid waste, carbonaceous agricultural material, carbonaceous forestry material, carbonaceous wood waste, carbonaceous construction material, carbonaceous vegetative material, carbonaceous petrochemical coproducts, coal, tires, plastics or their combinations. Further, as an embodiment, the present invention provides a method wherein said gasifier comprises one or more chambers, and can optionally comprise two chambers. The method of the present invention provides an embodiment wherein said gasifier comprises two chambers; further comprising injecting oxygen and carbon dioxide gas in first chamber; comprising injecting oxygen and carbon dioxide gas in second chamber; and injecting oxygen and carbon dioxide in both first and second chamber. It is contemplated that multiple chambers of a gasifier can optionally comprise further injection of oxygen and carbon dioxide gas in one or more successive chambers.

BRIEF DESCRIPTION OF THE FIGURES

FIG. 1 is a schematic diagram illustrating an embodiment of the role of carbon dioxide in biomass gasification overall process flow contemplated during normal operations of the present invention (lower chamber).

FIG. 2 is a schematic diagram illustrating an embodiment of the role of carbon dioxide in biomass gasification overall process flow contemplated during normal operations of the present invention (upper chamber).

FIG. 3 is a schematic diagram illustrating an embodiment of the role of carbon dioxide in biomass gasification overall process flow contemplated during normal operations of the present invention (multiple chambers).

FIG. 4 is a schematic diagram illustrating embodiments of the process synergies between the present invention and corn ethanol process.

FIG. 5 is a schematic diagram illustrating embodiments of the present invention providing a graphic illustration of total ethanol versus $CO_2$ added comparing multiple stage gasifier data and single stage gasifier data.

FIG. 6 is a schematic diagram illustrating embodiments of the present invention providing a graphic illustration of total ethanol versus $CO_2$ added.

FIG. 7 is a schematic diagram illustrating embodiments of the present invention providing a graphic illustration of $H_2/CO$ ratio versus $CO_2$ added comparing multiple stage gasifier data with single stage gasifier data.

FIG. 8 is a schematic diagram illustrating embodiments of the present invention providing a graphic illustration of $H_2/CO$ ratio versus $CO_2$ added

DETAILED DESCRIPTION OF THE INVENTION

Definitions

Unless otherwise defined, the following terms as used throughout this specification for the present invention are defined as follows and can include either the singular or plural forms of definitions below defined:

The term "about" modifying any amount refers to the variation in that amount encountered in real world conditions of sustaining microorganism culture, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in an multiple experiments in the plant or lab and the variation inherent in the analytical method. Whether or not modified by "about," the amounts include equivalents to those amounts. Any quantity stated herein and modified by "about" can also be employed in the present invention as the amount not modified by "about."

Unless stated otherwise, the term "acetate" is used to describe the mixture of molecular or free acetic acid and acetate salt present in the fermentation broth. The ratio of molecular acetic acid to acetate is dependent upon the pH of the system, i.e., at a constant "acetate" concentration, the lower the pH, the higher the molecular acetic acid concentration relative to acetate salt.

The term "acetogen" or "acetogenic" refers to a bacterium that generates acetate as a product of anaerobic respiration. This process is different from acetate fermentation, although both occur in the absence of oxygen and produce acetate. These organisms are also referred to as acetogenic bacteria, since all known acetogens are bacteria. Acetogens are found in a variety of habitats, generally those that are anaerobic (lack oxygen). Acetogens can use a variety of compounds as sources of energy and carbon; the best studied form of acetogenic metabolism involves the use of carbon dioxide as a carbon source and hydrogen as an energy source.

The term "biocatalyst" means, for the present invention, natural catalysts, protein enzymes, living cells, microorganisms, and bacteria.

The terms "bioreactor," "reactor," or "fermentation bioreactor," include a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas lift Fermenter, Static Mixer, or other device suitable for gas-liquid contact. Preferably for the method of this invention, the fermentation bioreactor comprises a growth reactor which feeds the fermentation broth to a second fermentation bioreactor, in which most of the product, ethanol, is produced.

"Carbonaceous material" as used herein refers to carbon rich material such as coal, and petrochemicals. However, in this specification, carbonaceous material includes any carbon material whether in solid, liquid, gas, or plasma state. Among the numerous items that can be considered carbonaceous material, the present invention contemplates: carbonaceous liquid product, carbonaceous industrial liquid recycle, carbonaceous municipal solid waste, carbonaceous agricultural material, carbonaceous forestry material, carbonaceous wood waste, carbonaceous construction material, carbonaceous vegetative material, carbonaceous industrial waste, carbonaceous fermentation waste, carbonaceous petrochemical coproducts, carbonaceous alcohol production coproducts, coal, tires, plastics, ethanol coproducts, spent grain, spent microorganisms, or their combinations.

"Cell concentration" in this specification is based on dry weight of bacteria per liter of sample. Cell concentration is measured directly or by calibration to a correlation with optical density.

The term "continuous method" as used herein refers to a fermentation method which includes continuous nutrient feed, substrate feed, cell production in the bioreactor, cell removal (or purge) from the bioreactor, and product removal. This continuous feeds, removals or cell production may occur in the same or in different streams. A continuous process results in the achievement of a steady state within the bioreactor. By "steady state" is meant that all of these measurable variables (i.e., productivity, feed rates, substrate and nutrient concentrations maintained in the bioreactor, cell concentration in the bioreactor and cell removal from the bioreactor, product removal from the bioreactor, as well as conditional variables such as temperatures and pressures) are constant over time.

"Ethanol productivity" is the volumetric productivity of ethanol, calculated as the ratio of the steady state ethanol concentration and the liquid retention time (LRT) in continuous systems, or the ratio of the ethanol concentration and the time required to produce that concentration in batch systems.

The phrase "high ethanol productivity" describes a volumetric ethanol productivity of greater than 10 g/L day.

"Excess $H_2$" is available for ethanol production when the ratio of the moles of $H_2$ in the feed gas to the sum of two times the moles of CO converted and three times the moles of $CO_2$ converted is greater than 1.0. If this ratio is less than 1.0, excess $H_2$ is not available and ethanol can only be produced through a different controlling mechanism.

The term "fermentation" means fermentation of CO to alcohols and acetate. A number of anaerobic bacteria are known to be capable of carrying out the fermentation of CO to alcohols, including butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, and *Clostridium autoethanogenum* (Aribini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). The disclosures of each of these publications are fully incorporated herein by reference. In addition, other acetogenic anaerobic bacteria may be selected for use in the process of the invention by a person of skill in the art. It will also be appreciated that a mixed culture of two or more bacteria may be used in the process of the present invention. One microorganism suitable for use in the present invention is *Clostridium autoethanogenum* that is available commercially from DSMZ and having the identifying characteristics of DSMZ deposit number DSMZ 10061. The fermentation may be carried out in any suitable bioreactor, such as a continuous stirred tank reactor (CTSR), a bubble column reactor (BCR) or a trickle bed reactor (TBR). Also, in some preferred embodiments of the invention, the bioreactor may comprise a first, growth reactor in which the microorganisms are cultured, and a second, fermentation reactor, to which fermentation broth from the growth reactor is fed and in which most of the fermentation product (ethanol and acetate) is produced.

The term "gaseous substrates" as used herein means CO alone, CO and $H_2$, $CO_2$ and $H_2$, or CO, $CO_2$ and $H_2$, optionally mixed with other elements or compounds, including nitrogen and hydrocarbons in a gaseous state. Such gaseous substrates include gases or streams, which are typically released or exhausted to the atmosphere either directly or through combustion. In some embodiments of this method the gaseous substrate comprises CO. In other embodiments of this method, the gaseous substrate comprises $CO_2$ and $H_2$. In still other embodiments, the gaseous substrate comprises CO and $H_2$. In a particularly preferred embodiment, the gaseous substrate comprises CO, $CO_2$ and $H_2$. Still other substrates of the invention may include those components mentioned above and at least one gas of nitrogen, $CO_2$, hydrocarbons, ethane and methane. Thus, such substrates include what is conventionally referred to as "syngas" or synthesis gas from the gasification of solid, liquid, or gaseous carbon products (including methane), as well as waste gases from a variety of industrial methods.

"Gasifier" means counter-current fixed bed gasifer, co-current fixed bed gasifier, moving bed, fluidized bed gasifier, entrained flow gasifier, plasma arc gasifier, single stage gasifier, multistage gasifier, two stage gasifier, three stage gasifer, four stage gasifier, five stage gasifer, and their combinations.

The phrase "high concentration of ethanol" means greater than about 10 g/L, preferably greater than 15 g/L ethanol in fermentation broth or a product ratio of ethanol to acetate of 5:1 or more.

The terms "limiting substrate" or "limiting nutrient" define a substance in the nutrient medium or gaseous substrate which, during bacterial culture growth in the bioreactor, is depleted by the culture to a level which no longer supports steady state or stable bacterial growth in the bioreactor. All other substances in the nutrient medium or gas substrate are thus present in excess, and are "non-limiting". The evidence for limitation is that an increase in the rate of addition of the limiting substrate, i.e. in the nutrient feed rate or gas feed rate, to the culture causes a corresponding increase in the rate of gas uptake (mmol/min of gas) due to increase in cell density or cell metabolism.

The term "microorganism" includes bacteria, fungi, yeast, archaea, and protists; microscopic plants (called green algae); and animals such as plankton, the planarian and the amoeba. Some also include viruses, but others consider these as non-living. Microorganisms live in all parts of the biosphere where there is liquid water, including soil, hot springs, on the ocean floor, high in the atmosphere and deep inside rocks within the Earth's crust. Microorganisms are critical to nutrient recycling in ecosystems as they act as decomposers. Microbes are also exploited by people in biotechnology, both in traditional food and beverage preparation, and in modern technologies based on genetic engineering. It is envisioned that mixed strain microorganisms, that may or may not contain strains of various microorganisms, will be utilized in the present invention. Also, it is envisioned that directed evolution can selectively screen microorganisms that can be utilized in the present invention. It is further envisioned that recombinant DNA technology can create microorganisms using select strains of existing microorganisms. It is envisioned that acetogenic anaerobic (or facultative) bacteria, which are able to convert CO and water or $H_2$ and $CO_2$ into ethanol and acetic acid products will be utilized in the present invention. Useful bacteria according to this invention include, without limitation, *Acetogenium kivui*, *Acetobacterium woodii*, *Acetoanaerobium noterae*, *Butyribacterium methylotrophicum*, *Caldanaerobacter subterraneus*, *Caldanaerobacter subterraneus pacificus*, *Carboxydothermus hydrogenoformans*, *Clostridium aceticum*, *Clostridium acetobutylicum*, *Clostridium Autoethanogenum*, *Clostridium thermoaceticum*, *Eubacterium limosum*, *Clostridium ljungdahlii* PETC, *Clostridium ljungdahlii* ER12, *Clostridium ljungdahlii* C-01, *Clostridium ljungdahlii* O-52, *Clostridium ultunense*, *Clostridium ragsdalei*, *Clostridium carboxidivorans*, *Geobacter sulfurreducens*, *Moorella*, *Moorella thermacetica*, and *Peptostreptococcus productus*. Other acetogenic anaerobic bacteria are selected for use in these methods by one of skill in the art. In some embodiments of the present invention, several exemplary strains of *C. ljungdahlii* include strain PETC (U.S. Pat. No. 5,173,429); strain ER12 (U.S. Pat. No. 5,593,886) and strains C-01 and O-52 (U.S. Pat. No. 6,136,577). These strains are each deposited in the American Type Culture Collection, 10801 University Boulevard, Manassas, Va. 20110-2209, under Accession Nos.: 55383 (formerly ATCC No. 49587), 55380, 55988, and 55989 respectively. Each of the strains of *C. ljungdahlii* is an anaerobic, gram-positive bacterium with a guanine and cytosine (G+C) nucleotide content of about 22 mole %. These bacteria use a variety of substrates for growth, but not methanol or lactate. These strains differ in their CO tolerance, specific gas uptake rates and specific productivities. In the "wild" strains found in nature, very little ethanol production is noted. Strains of *C. ljungdahlii* operate ideally at 37.degree. C., and typically produce an ethanol to acetyl (i.e. which refers to both free or molecular acetic acid and acetate salts) product ratio of about 1:20 (1 part ethanol per 20 parts acetyl) in the "wild" state. Ethanol concentrations are typically only 1-2 g/L. While this ability to produce ethanol is of interest, because of low ethanol productivity the "wild" bacteria cannot be used to economically produce ethanol on a commercial basis. With minor nutrient manipulation the above-mentioned *C. ljungdahlii* strains have been used to produce ethanol and acetyl with a product ratio of 1:1 (equal parts ethanol and acetyl), but the ethanol concentration is less than 10 g/L, a level that results in low productivity, below 10 g/L.day. In addition culture stability is an issue, primarily due to the relatively high (8-10 g/L) concentration of acetyl (2.5-3 g/L molecular acetic acid) in combination with the presence of ethanol. Furthermore, as the gas rate is increased in an effort to produce more ethanol, the culture is inhibited, first by molecular acetic acid and then by CO. As a result, the culture becomes unstable and fails to uptake gas and produce additional product. Further, early work by the inventors showed difficulty in producing more than a 2:1 ratio of ethanol to acetyl in a steady state operation. See, e.g., Klasson et al., 1990 Applied Biochemistry and Biotechnology, Proceedings of the 11.sup.th Symposium on Biotechnology for Fuels and Chemicals, 24/25: 857; Phillips et al., 1993 Applied Biochemistry and Biotechnology, Proceedings of the 14.sup.th Symposium on Biotechnology for Fuels and Chemicals, 39/40: 559, among others. A large number of documents describe the use of anaerobic bacteria, other than *C. ljungdahlii*, in the fermentation of sugars that do not consume CO, $CO_2$ and $H_2$ to produce solvents. In an attempt to provide high yields of ethanol, a variety of parameters have been altered which include: nutrient types, microorganism, specific addition of reducing agents, pH variations, and the addition of exogenous gases. See, e.g., Rothstein et al, 1986 J. Bacteriol., 165(1):319-320; Lovitt et al, 1988 J. Bacteriol., 170(6):2809; Taherzadeh et al, 1996 Appl. Microbiol. Biotechnol., 46:176.

By the term "mixed strains," it is meant a mixed culture of two or more of the microorganisms or biocatalysts. Such "mixed strains" of the microorganisms or biocatalysts enumerated hereinabove are utilized in the methods of this invention. It is envisioned that directed evolution, genetically modified techniques, or other similar methods can result in mixed stain cultures for use in the present invention.

The term "natural state" describes any compound, element, or pathway having no additional electrons or protons that are normally present. Conversely, the term "reduction state" describes any compound, element, or pathway having an excess of one or more electrons. The "reduction state" is achieved by adding one or more electrons to the "natural state", i.e. by lowering the redox potential of the fermentation broth.

"Nutrient medium" is used generally to describe conventional bacterial growth media which contain vitamins and minerals sufficient to permit growth of a selected subject bacteria. Sugars are not included in these media. Components of a variety of nutrient media suitable to the use of this invention are known and reported in prior publications, including those of the inventors. See, e.g. the nutrient media formulae described in International Patent Application No. WO08/00558; U.S. Pat. Nos. 5,807,722; 5,593,886, and 5,821,111, as well as in the publications identified above.

According to the present invention, a typical laboratory nutrient medium for acetate production from CO, $CO_2$, and $H_2$ contains 0.9 mg/L calcium pantothenate. However, a typical laboratory nutrient medium for ethanol production from CO, $CO_2$, and $H_2$ contains 0.02 mg/L calcium pantothenate.

The term "reducing gas" means either or both CO or $H_2$. By the phrase "an amount of reducing gas greater than that required for growth of the bacteria' is meant that amount of reducing gas that exceeds the amount that the bacteria can use for growth or metabolism, given the nutrient medium ingredients. This amount can be achieved by increasing the net amount of reducing gas, or by reducing key nutrient ingredients, so that the excess amount of gas is achieved without increasing the gas, or by increasing the rate of gas delivery to the bacteria. When the bacteria are exposed to more reducing gas than required for growth, the bacteria respond by increasing the production of ethanol. "Subject bacteria" are microorganisms or acetogenic anaerobic (or facultative) bacteria, which are able to convert CO and water or $H_2$ and $CO_2$ into ethanol and acetic acid products.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is also used as an intermediate in producing synthetic petroleum for use as a fuel or lubricant via Fischer-Tropsch synthesis and previously the Mobil methanol to gasoline process. Syngas consists primarily of hydrogen, carbon monoxide, and very often some carbon dioxide, and has less than half the energy density (i.e., BTU content) of natural gas. Syngas is combustible and often used as a fuel source or as an intermediate for the production of other chemicals.

DETAILED DESCRIPTION OF THE PRESENT INVENTION UTILIZING CARBON DIOXIDE IN BIOMASS GASIFICATION

The present disclosure will now be described more fully with reference to the Figures in which various embodiments of the present invention are shown. The subject matter of this disclosure may, however, be embodied in many different forms and should not be construed as being limited to the embodiments set forth herein.

FIG. 1 shows a schematic of an example of a biomass gasifier with oxygen or air and carbon dioxide feed under the char bed according to one embodiment of the present invention. FIG. 2 shows a schematic of an example of a biomass gasifier with oxygen or air and carbon dioxide feed in an upper chamber of the gasifer as one embodiment of the present invention. FIG. 3 shows a schematic of an example of a biomass gasifier with oxygen or air and carbon dioxide feed under the char bed and oxygen or air and carbon dioxide feed in an upper chamber of the gasifer as one embodiment of the present invention. As an embodiment, multiple stage gasifiers with multiple chambers contain further embodiments of the present invention.

The carbon dioxide serves two purposes. The addition of carbon dioxide ($CO_2$) to the oxidant introduced into the gasifier has been shown to control the problem of slagging by providing a heat sink to reduce the temperature. Visual observations during preliminary experiments has indicated a reduction in ash slagging.

Secondly, the externally introduced CO2 reacts with carbon (char), H2 and hydrocarbons (such as methane), according to equations 3-5 above, in the gasifier to produce additional carbon monoxide (CO) and/or hydrogen. This can result in additional alcohol (such as ethanol) production according to equations 1 and 2 above. Preliminary gasification experiments with wood chips has shown the potential for shifting externally fed carbon dioxide to carbon monoxide, as noted in Table 1. The preliminary experimental data shows the ratio of carbon monoxide to hydrogen increases with increasing carbon dioxide feed rate. The hydrogen and CO production rates from gasification should be reasonably constant with the same biomass and oxygen feed rates. Since the gas flow rate is increasing slightly, and the CO/H2 ratio is increasing, CO2 is being reformed (shifted) to CO.

TABLE 1

Data for Wood Gasification with Oxygen and Externally Introduced Carbon Dioxide

| Biomass (lbs/hr) | Oxygen (lbs/hr) | CO2 added (lbs/hr) | H (lb-mol/DT) | CO (lb-mol/DT) | CO/H2 |
|---|---|---|---|---|---|
| 103 | 9.6 | 0 | 19.04 | 31.25 | 1.64 |
| 117 | 9.7 | 5 | 20.85 | 35.13 | 1.68 |
| 104 | 9.7 | 10 | 18.81 | 31.13 | 1.74 |
| 111 | 9.6 | 15 | 16.51 | 32.04 | 1.94 |
| 106 | 9.6 | 20 | 15.34 | 30.80 | 2.01 |

Additional experimentation to optimize the oxidant to biomass and the carbon dioxide to oxygen ratios, in addition to other gasification parameters, should result in improved carbon monoxide production from externally introduced carbon dioxide. It is envisioned that a CO2 to O2 ratio of oxidizing gas fed under the biomass/char material would range from a ratio of zero to 4 by weight. The above experiments used a range of zero to 2.08 weight ratio. The use of CO2 as oxidant reduces the quantity of O2 normally used for gasification. The composition of CO is also increased, enhancing subsequent reactions of the syngas. Perhaps, most importantly, the CO2 emitted to the environment will be reduced.

FIG. 5 comprises embodiments of the present invention providing a graphic illustration of total ethanol produced versus CO2 added comparing multiple stage gasifier data and single stage gasifier data. FIG. 5 comprises embodiments of the present invention providing a graphic illustration of total ethanol (Gal/DT) versus CO2 (lbsmole/DT) added comparing multiple stage gasifier data and single stage gasifier data. In one embodiment, FIG. 5 shows the data of a two stage gasifier wherein the carbon dioxide is added to a lower chamber (LC). In another embodiment, FIG. 5 shows the data of a two stage gasifier wherein the carbon dioxide is added to a upper chamber (UC). In an embodiment, FIG. 5 shows the data of a single stage gasifier wherein carbon dioxide is added (1S). No steam has been added to the gasifiers. It is believed that steam addition in the lower chamber may create a different base case. In normal operating conditions, steam is added to the lower chamber in order to facilitate the gasification process however addition of steam in the lower chamber reduces the ethanol production. It is believed, a base case corresponding to steam addition to the lower chamber would be expected to have a lower ethanol yield for example for 12.3 lbsmole steam/DT in the lower chamber an estimated ethanol yield is about 80.5 Gal/DT). Therefore, it is believed, that substituting CO2, for steam, in the lower chamber comprises an embodiment of the present invention.

FIG. 6 comprises embodiments of the present invention providing a graphic illustration of Total Ethanol versus CO2 added. FIG. 6 comprises embodiments of the present invention providing a graphic illustration of total ethanol gallons per dry ton (Gal/DT) versus CO2 pound mole per dry ton (lbsmole/DT) added. FIG. 6 comprises embodiments wherein CO2 is added to a lower and upper chamber. FIG. 6 comprises embodiments wherein 15 lb-mole/DT CO2 comprises adding to a lower and comprises adding a variable range of CO2, 0-30 lb-mole/DT, to the upper chamber.

FIG. 7 comprises embodiments of the present invention providing a graphic illustration of hydrogen to carbon monoxide ratio (H2/CO) versus carbon dioxide (CO2) added comparing multiple stage gasifier data with single stage gasifier data. FIG. 7 comprises embodiments of the present invention providing a graphic illustration of H2/CO ratio versus CO2 pound mole per dry ton (lbsmole/DT) added comparing multiple stage gasifier data with single stage gasifier data. In one embodiment, FIG. 7 provides the illustration of data of a two stage gasifier of the hydrogen to carbon monoxide (H2/CO) ratio and carbon dioxide added to a lower chamber (LC). In another embodiment, FIG. 7 provides the illustration of data of a two stage gasifier of the hydrogen to carbon monoxide (H2/CO) ratio and carbon dioxide added to a upper chamber (UC). It should be noted that in this illustration multiple stage gasifier data comprises substantially overlapping data. In FIG. 7 the data in CO2 in LC—2 Stage and CO2 in UC—2 Stage are substantially overlapping.

FIG. 8 comprises embodiments of the present invention providing a graphic illustration of hydrogen to carbon monoxide ration (H2/CO) versus carbon dioxide (CO2) added. FIG. 8 comprises embodiments of the present invention providing a graphic illustration of H2/CO ratio versus CO2 pound mole per dry ton (lbsmole/DT) added. FIG. 8 comprises embodiments wherein 15 lb-mole/DT CO2 comprises adding to a lower and comprises adding a variable range of CO2, 0-30 lb-mole/DT, to the upper chamber.

The present invention contemplates methods of optimizing syngas production via gasification of carbonaceous material in a gasifier comprising: injecting carbon dioxide gas, oxygen, and carbonaceous material into a gasifier; creating syngas comprising carbon monoxide and hydrogen. Wherein said carbonaceous material comprises selection from: carbonaceous material, carbonaceous liquid product, industrial carbonaceous liquid recycle, carbonaceous municipal solid waste, carbonaceous agricultural material, carbonaceous forestry material, carbonaceous wood waste, carbonaceous construction material, carbonaceous vegetative material, carbonaceous petrochemical coproducts, carbonaceous coal, tires or their combinations. As an embodiment, said gasifier comprises one or more chambers; said gasifier comprises two chambers; said gasifier comprises two chambers; further comprising injecting carbon dioxide and oxygen gas in first chamber; comprising injecting carbon dioxide and oxygen gas in second chamber; and injecting carbon dioxide and oxygen in both first and second chamber. As a further embodiment said gasifier comprises two chambers; further comprising injecting up to 50 lb-moles carbon dioxide per DT of said carbonaceous material in first chamber; said gasifer comprises two chambers; further comprising injecting up to 50 lb-moles carbon dioxide per DT said carbonaceous material in second chamber; said gasifier comprises two chambers; further comprising injecting up to 50 lb-moles carbon dioxide per DT of said carbonaceous material in first chamber; comprising injecting up to 50 lb-moles carbon dioxide per DT of said carbonaceous material in second chamber. The syngas of the present invention comprises a hydrogen to carbon monoxide ratio of three or less; comprises a hydrogen to carbon monoxide ratio of one or less.

As another embodiment, the present invention provides method of producing alcohol comprising: contacting syngas with biocatalyst in a fermentation container to produce an alcohol product mixture; selectively recovering alcohol from the product mixture. The present invention contemplates alcohol production of: methanol; ethanol; propanol; and/or butanol; or their combinations. As an embodiment, said biocatalyst comprises: microoganisms; acetogenic bacteria; one or more strains selected from *Clostridium, Moorella*, and *Carboxydothermus* or their mixed strains; *Clostridium ljungdahlii*. Said *Clostridium ljungdahlii* of the present invention is selected from the strains consisting of PETC, ERI-2, O-52 and C-01 or their combinations.

As a further embodiment, the present invention contemplates methods of producing alcohol comprising: injecting carbon dioxide and oxygen gas and carbonaceous material into a gasifier; creating syngas comprising carbon monoxide and hydrogen; contacting syngas with biocatalyst in a fermentation container to produce an alcohol product mixture; selectively recovering alcohol from the product mixture.

The foregoing descriptions of specific embodiments of the present invention are presented for purposes of illustration and description. They are not intended to be exhaustive or to limit the invention to the precise forms disclosed. Obviously, many modifications and variations are possible in view of the above teachings. While the embodiments were chosen and described in order to best explain the principles of the invention and its practical applications, thereby enabling others skilled in the art to best utilize the invention, various embodiments with various modifications as are suited to the particular use are also possible.

DETAILED DESCRIPTION OF THE PRESENT INVENTION DESCRIBING INTEGRATION OF GASIFICATION AND FERMENTATION PROCESSES WITH SUGAR FERMENTATION TO ETHANOL PROCESSES

The present disclosure will now be described more fully with reference to the Figures in which various embodiments of the present invention are shown. The subject matter of this disclosure may, however, be embodied in many different forms and should not be construed as being limited to the embodiments set forth herein.

Production of ethanol from biomass has been demonstrated by a process which first gasifies the carbonaceous matter and then ferments the carbon monoxide and hydrogen in the syngas into ethanol. This process has waste heat from cooling the hot syngas before fermentation and from burning the unconverted syngas. This waste heat can be used to generate steam and electricity for internal process needs and/or exported.

It is comtemplated by the present invention that locating the biomass and sugar ethanol plants adjacent to one another allows for the full utilization of all the energy available from the crop. In the embodiments illustrated in FIG. 4, for example, the farmer may bring corn to the ethanol plant and may also bring the corn stover, which would enable additional ethanol production with no purchased fuel or electricity by either facility. Other advantageous synergies between these processes include combining ethanol purification equipment and use of common ethanol storage and loadout facilities, utilities, maintenance facilities, offices, laboratories, and other types of equipment and facilities known in the art to be associated with ethanol storage and production.

A typical corn ethanol plant, for example, requires about 1.2 KWH of electricity and about 25,000 to about 37,000 Btu of thermal energy per gallon of ethanol produced. It is believed that the gasification and/or fermentation plant of the present invention allows all or much of the electricity and steam to operate the plant from the process waste heat. In addition, this process can produce about an additional 2.5 KWH per gallon for export. Exhaust steam from the power generation cycle could provide almost about 60,000 Btu per gallon. Hence it is believed, co-location of these facilities provides enough waste energy from the biomass to operate both plants. An additional economic benefit would be available to the farmer from the sale of the crop residue. Utilization of the entire crop will maximize energy efficiencies and minimize emission of global warming gases.

As an embodiment, said carbon dioxide gas is obtained from a corn to ethanol facility. Said carbonaceous material of the present invention comprises selection from: corn, corn stover, corn cobs, corn kernels, corn kernel fragments, corn plant fragments, fermentation waste, spent grain, spent microorganisms, spent biocatalyst, alcohol production liquid recycle, corn co-products, alcohol co-products, ethanol co-products, or their combinations. The present invention further comprises producing steam used for utilization by a corn to ethanol facility. The present invention further comprises producing electricity used for utilization by a corn to ethanol facility. It is envisioned that the present invention further comprises sequestration of carbon dioxide; sequestration of carbon dioxide from a gaseous stream for carbon dioxide conversion to alcohol. The present invention further contemplates a method of optimizing syngas production via gasification of carbonaceous material in a gasifier comprising: injecting carbon dioxide gas, oxygen, and carbonaceous material into a gasifier; creating syngas comprising carbon monoxide and hydrogen; further comprising producing alcohol comprising: contacting syngas with biocatalyst in a fermentation container to produce an alcohol product mixture; selectively recovering alcohol from the product mixture.

The foregoing descriptions of specific embodiments of the present invention are presented for purposes of illustration and description. They are not intended to be exhaustive or to limit the invention to the precise forms disclosed. Obviously, many modifications and variations are possible in view of the above teachings. While the embodiments were chosen and described in order to best explain the principles of the invention and its practical applications, thereby enabling others skilled in the art to best utilize the invention, various embodiments with various modifications as are suited to the particular use are also possible.

EXAMPLES

A multistage gasifier is contemplated in the present invention. The following examples utilize a two stage gasifier that is similar to a Consutech two stage combustor modified to operate as a gasifier with an object to maximize carbon monoxide and hydrogen production while minimizing other constituents in product syngas. Carbonaceous material is fed to the first stage (lower chamber) in which air, oxygen-enriched air or pure oxygen can be injected at a controlled rate below a grate. The first stage temperature and oxygen input is controlled such that only partial oxidation of carbonaceous material occurs, not complete combustion (also described as starved air or starved oxygen combustion). A temperature of about 1400 degrees F. is maintained in the first stage. In one embodiment, a temperature lower than about 1400 degrees F. can be maintained in the first stage; a temperature in the range of about 750 to about 1400 degrees F. can be maintained in the first stage. The gaseous product from the first stage (lower chamber) moves to the second stage (upper chamber). Ash is removed from the first stage. Pure oxygen is introduced into the second stage to raise the temperature to about 1750 to about 2250 degrees F. in the second stage in order to accomplish cracking and partial oxidation of any tar (such as heavy hydrocarbons) contained in the gaseous stream from the first stage. A raw producer or synthesis gas (syngas) containing CO, H2 CO2, N2 and other constituents (e.g., O2, particulate matter (PM), tars, metals) is produced and removed from second stage. In one embodiment, steam can be injected in the first stage or lower chamber. In an embodiment, steam can be injected in the second stage or upper chamber. In another embodiment, carbon dioxide can be injected in the second chamber; carbon dioxide can be injected in the first chamber.

A one stage gasifier used for the examples to follow introduces carbonaceous material and air, oxygen-enriched air or pure oxygen in one single chamber. A temperature of about 2250 degrees F. is maintained in the gasifier chamber. A raw producer or synthesis gas (syngas) containing CO, $H_2CO2$, N2 and other constituents is produced and removed from the gasifier chamber. In one embodiment, steam can be injected in the gasifier. In another embodiment, carbon dioxide can be injected in the gasifier.

Following gasification, the producer gas is subject to cleanup. Gas cleaning at the pilot plant consists of cooling with a water spray column directly after the gasifier. The water scrubbing at about 100 degrees F. is sufficient to clean gas for fermenter requirements. The scrubber water requires treatment, but simple mechanical filtering of the water is sufficient because the carbon in the PM scrubbed out of the gas absorbs enough of the contaminants in the scrubber water that it can be considered dischargeable if the solids are removed. This wet filtrate can be sent back to the gasifier, and the water discharged. A cyclone separator removes PM and droplets.

The product syngas is introduced in a bioreactor to produce alcohols; methanol; ethanol; propanol; and/or butanol.

Comparative Example 1

2-Stage Gasifier (Multi-Stage Gasifier)

In this example oxygen is introduced in the first and second stages as follows in order to attain temperatures of 1400 and 2250 degrees F. in the first and second stage respectively. A product syngas and ethanol product is obtained as follows in Table 2:

TABLE 2

Data for Comparative Example 1

| | Amount, lb-mole/DT |
|---|---|
| Feed: | |
| O2 in $1^{st}$ stage | 12.316 |
| O2 in $2^{nd}$ stage | 14.0376 |
| Product: | |
| H2 | 47.6608 |
| CO | 62.6862 |
| CO2 | 14.2429 |
| H2O | 28.1103 |
| EtOH (1) | 83.2969 |

TABLE 2-continued

Data for Comparative Example 1

| | Amount, lb-mole/DT |
|---|---|
| EtOH (1)* | 80.5 |
| H2/CO (2) | 0.760 |

(1) in gal/DT
(2) in lb-mole/lb-mole
*contains 12.3 lb-mole/DT steam in lower chamber

Examples 1-7

2-Stage Gasifier with CO2 Injected in the First Stage (Lower Chamber)

In this example oxygen is introduced in the first and second stages as follows in order to attain temperatures of 1400 and 2250 degrees F. in the first and second stage respectively. Carbon dioxide is introduced in the first stage (lower chamber) as indicated in the Table 3. Product syngas and ethanol product is obtained as in the table below.

Examples 8-14

2-Stage Gasifier with CO2 Injected in the Second Stage (Upper Chamber)

In this example, oxygen is introduced in the first and second stages as follows in order to attain temperatures of 1400 and 2250 degrees F. in the first and second stage respectively. Carbon dioxide is introduced in the second stage (upper chamber) as indicated in the table below. Product syngas and ethanol product is obtained as in the Table 4.

Examples 15-20

2-Stage Gasifier with CO2 Injected in Both the First Stage (Lower Chamber) and Second Stage (Upper Chamber)

In this example oxygen is introduced in the first and second stages as follows in order to attain temperatures of 1400 and 2250 degrees F. in the first and second stage respectively. Carbon dioxide is introduced in both the first stage (lower chamber) and second stage (upper chamber) as indicated in the table below. Product syngas and ethanol product is obtained as in Table 5.

Comparative Example 2

1-Stage Gasifier

In this example oxygen is introduced as follows in order to attain temperature of 2250 degrees F. in gasifier. A product syngas and ethanol product is obtained as follows in Table 6 below:

TABLE 6

Data for Comparative Example 2

| Component | Amount, lb-mole/DT |
|---|---|
| Feed: | |
| O2 | 24.6821 |
| Product: | |
| H2 | 44.1748 |
| CO | 60.7823 |
| CO2 | 16.7413 |
| H2O | 31.5813 |
| EtOH (1) | 79.8673 |
| H2/CO (2) | 0.727 |

(1) in gal/DT
(2) in lb-mole/lb-mole

Examples 21-27

1-Stage Gasifier with CO2 Injection

In this example oxygen is introduced in the gasifier as follows in order to attain temperature of 2250 degrees F. in the gasifier. Carbon dioxide is introduced in the gasifier as indicated in Table 7. Product syngas and ethanol product is obtained as in the table below.

All published documents are incorporated by reference herein. Numerous modifications and variations of the present invention are included in the above-identified specification and are expected to be obvious to one of skill in the art. Such modifications and alterations to the compositions and methods of the present invention are believed to be encompassed in the scope of the claims appended hereto.

TABLE 3

Data for Examples 1-7

| | Amount, lb-mole/DT | | | | | | |
|---|---|---|---|---|---|---|---|
| Component | Ex-1 | Ex-2 | Ex-3 | Ex-4 | Ex-5 | Ex-6 | Ex-7 |
| Feed: | | | | | | | |
| CO2 added | 5 | 10 | 15 | 20 | 30 | 40 | 50 |
| O2 in $1^{st}$ stage | 13.1927 | 14.0162 | 14.8061 | 15.557 | 16.9788 | 18.304 | 19.5574 |
| O2 in $2^{nd}$ stage | 14.0126 | 14.0194 | 14.0457 | 14.0935 | 14.2312 | 14.4194 | 14.6414 |
| Product: | | | | | | | |
| H2 | 44.3829 | 41.3818 | 38.628 | 36.111 | 31.6938 | 27.9797 | 24.8378 |
| CO | 64.4059 | 65.8829 | 67.1251 | 68.1625 | 69.6868 | 70.5914 | 70.9788 |
| CO2 | 17.5458 | 21.09 | 24.8593 | 28.8338 | 37.3292 | 46.443 | 56.0659 |
| H2O | 31.3842 | 34.3856 | 37.1367 | 39.6512 | 44.0689 | 47.7883 | 50.929 |

TABLE 3-continued

Data for Examples 1-7

Amount, lb-mole/DT

| Component | Ex-1 | Ex-2 | Ex-3 | Ex-4 | Ex-5 | Ex-6 | Ex-7 |
|---|---|---|---|---|---|---|---|
| ETOH (1) | 83.5580 | 83.7002 | 83.7184 | 83.6377 | 83.2018 | 82.4607 | 81.4586 |
| H2/CO (2) | 0.689 | 0.628 | 0.575 | 0.530 | 0.455 | 0.396 | 0.350 |

(1) in gal/DT
(2) in lb-mole/lb-mole

TABLE 4

Data for Examples 8-14

Amount, lb-mole/DT

| Component | Ex-8 | Ex-9 | Ex-10 | Ex-11 | Ex-12 | Ex-13 | Ex-14 |
|---|---|---|---|---|---|---|---|
| Feed: | | | | | | | |
| CO2 added | 5 | 10 | 15 | 20 | 30 | 40 | 50 |
| O2 in 1st stage | 12.316 | 12.316 | 12.316 | 12.316 | 12.316 | 12.316 | 12.316 |
| O2 in 2nd stage | 14.7942 | 15.5323 | 16.2543 | 16.9613 | 18.3377 | 19.6715 | 20.9708 |
| Product: | | | | | | | |
| H2, | 44.4973 | 41.5935 | 38.9336 | 36.4926 | 32.1981 | 28.5721 | 25.4971 |
| CO | 64.4907 | 66.0582 | 67.4138 | 68.5632 | 70.3399 | 71.511 | 72.1931 |
| CO2 | 17.4608 | 20.9089 | 24.5735 | 28.4334 | 36.6751 | 45.5107 | 54.8373 |
| H2O | 31.2745 | 34.1752 | 36.8411 | 39.2828 | 43.5766 | 47.2016 | 50.276 |
| ETOH (1) | 83.6927 | 83.9678 | 84.1400 | 84.2041 | 84.0730 | 83.6356 | 82.9557 |
| H2/CO (2) | 0.690 | 0.630 | 0.578 | 0.532 | 0.458 | 0.400 | 0.353 |

(1) in gal/DT
(2) in lb-mole/lb-mole

TABLE 5

Data for Examples 15-20

Amount, lb-mole/DT

| Component | Ex-15 | Ex-16 | Ex-17 | Ex-18 | Ex-19 | Ex-20 |
|---|---|---|---|---|---|---|
| Feed: | | | | | | |
| Total CO2 added | 15 | 20 | 25 | 30 | 35 | 45 |
| CO2 in 1st stage | 15 | 15 | 15 | 15 | 15 | 15 |
| CO2 in 2nd stage | 0 | 5 | 10 | 15 | 20 | 30 |
| O2 in 1st stage | 14.8061 | 14.8061 | 14.8061 | 14.8061 | 14.8061 | 14.8061 |
| O2 in 2nd stage | 14.0457 | 14.7524 | 15.4441 | 16.1258 | 16.7981 | 18.1106 |
| Product | | | | | | |
| H2 | 38.628 | 36.2017 | 33.9834 | 31.9415 | 30.0655 | 26.7547 |
| CO | 67.1251 | 68.2586 | 69.2183 | 70.0099 | 70.651 | 71.5421 |
| CO2 | 24.9593 | 28.7338 | 32.7889 | 37.0074 | 41.3704 | 50.4855 |
| H2O | 37.1367 | 39.5597 | 41.7844 | 43.8264 | 45.7007 | 49.0104 |
| ETOH (1) | 83.7184 | 83.7731 | 83.7471 | 83.6320 | 83.4406 | 82.8642 |
| H2/CO (2) | 0.575 | 0.530 | 0.491 | 0.456 | 0.426 | 0.374 |

(1) in gal/DT
(2) in lb-mole/lb-mole

TABLE 7

Data for Examples 21-27

Amount, lb-mole/DT

| Component | Ex-21 | Ex-22 | Ex-23 | Ex-24 | Ex-25 | Ex-26 | Ex-27 |
|---|---|---|---|---|---|---|---|
| Feed: | | | | | | | |
| CO2 added | 5 | 10 | 15 | 20 | 30 | 40 | 50 |
| O2 added | 30.5188 | 31.3378 | 32.1391 | 32.9277 | 34.4177 | 35.9635 | 37.4267 |
| Product: | | | | | | | |
| H2 | 41.1093 | 38.3065 | 35.7479 | 33.4404 | 29.3004 | 25.853 | 22.9397 |
| CO | 62.3112 | 63.6041 | 64.68 | 65.5577 | 66.795 | 67.4491 | 67.6309 |
| CO2 | 20.232 | 23.955 | 27.8913 | 32.022 | 40.7998 | 50.1545 | 59.9858 |

TABLE 7-continued

Data for Examples 21-27

| Component | Amount, lb-mole/DT | | | | | | |
|---|---|---|---|---|---|---|---|
| | Ex-21 | Ex-22 | Ex-23 | Ex-24 | Ex-25 | Ex-26 | Ex-27 |
| H2O | 34.6481 | 37.452 | 40.0119 | 42.3536 | 46.4577 | 49.9023 | 52.8182 |
| ETOH (1) | 80.0326 | 80.0795 | 80.0186 | 79.8718 | 79.2732 | 78.4011 | 77.2957 |
| H2/CO (2) | 0.660 | 0.602 | 0.552 | 0.510 | 0.439 | 0.383 | 0.339 |

(1) in gal/DT
(2) in lb-mole/lb-mole

The invention claimed is:

1. A method of sequestration of carbon dioxide from a gaseous stream by improving syngas production via gasification of carbonaceous material to increase carbon monoxide production comprising: injecting carbon dioxide gas, oxygen, and carbonaceous material into a moving bed or fixed bed gasifier; wherein up to 50 lb-moles carbon dioxide per DT of said carbonaceous material is injected in one or more chambers of said gasifier; optionally, wherein at least a portion of the 50 lb-moles carbon dioxide per DT of said carbonaceous material is provided from waste gases from a variety of industrial methods; creating syngas comprising carbon monoxide and hydrogen; wherein said syngas comprises a hydrogen to carbon monoxide ratio of one or less; wherein increasing said carbon monoxide production at least 2.5%; wherein further comprising sequestration of carbon dioxide from a gaseous stream for carbon dioxide conversion to alcohol; contacting said syngas with biocatalyst to produce an alcohol product mixture comprising methanol, ethanol, propanol or butanol or their combinations; selectively recovering alcohol from the product mixture; wherein the process provides a volumetric ethanol productivity.

2. The method of claim 1, wherein said carbonaceous material is selected from the group consisting of carbonaceous material, carbonaceous liquid product, industrial carbonaceous liquid recycle, carbonaceous municipal solid waste, carbonaceous agricultural material, carbonaceous forestry material, carbonaceous wood waste, carbonaceous construction material, carbonaceous vegetative material, carbonaceous petrochemical coproducts, carbonaceous coal, tires and their combinations.

3. The method of claim 1, wherein said gasifier comprises one or more chambers.

4. The method of claim 1, wherein said gasifier comprises two chambers.

5. The method of claim 1, wherein said gasifier comprises two chambers; further comprising injecting carbon dioxide and oxygen gas in first of said two chambers; comprising injecting carbon dioxide and oxygen gas in second of said two chambers.

6. The method of claim 5 wherein said gasifer comprises two chambers; further comprising injecting up to 50 lb-moles carbon dioxide per DT of said carbonaceous material in second of said two chambers.

7. The method of claim 1, wherein said syngas comprises a hydrogen to carbon monoxide ratio of one or less.

8. The method of claim 1, wherein the ratio of CO2 added to (CO2 product -CO2 added) is greater than 0.33.

* * * * *

UNITED STATES PATENT AND TRADEMARK OFFICE
CERTIFICATE OF CORRECTION

| | | |
|---|---|---|
| PATENT NO. | : 8,592,190 B2 | Page 1 of 1 |
| APPLICATION NO. | : 12/456049 | |
| DATED | : November 26, 2013 | |
| INVENTOR(S) | : James L Gaddy et al. | |

It is certified that error appears in the above-identified patent and that said Letters Patent is hereby corrected as shown below:

In the Specification

Col. 1, line 10 insert-
--This invention was made with government support under Grant No. DE-FG36-04GO14315 awarded by the US Department of Energy. The government has certain rights in the invention.--

Signed and Sealed this
Sixteenth Day of September, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,592,190 B2 |
| APPLICATION NO. | : 12/456049 |
| DATED | : November 26, 2013 |
| INVENTOR(S) | : James L. Gaddy et al. |

It is certified that error appears in the above-identified patent and that said Letters Patent is hereby corrected as shown below:

Title Page

Item (73) Assignee:

Change "Ineos Bio Limited, Lisle, IL" to --Ineos Bio SA, Rolle, Switzerland--

Item (74) Attorney, Agent or Firm:

Change "Vikrant B. Pancha; Ineos Bio SA" to --Vikrant B. Panchal; Ineos Bio SA--

Signed and Sealed this
Eighteenth Day of November, 2014

Michelle K. Lee
*Deputy Director of the United States Patent and Trademark Office*